US012773475B2

(12) United States Patent
Griffin et al.

(10) Patent No.: US 12,773,475 B2
(45) Date of Patent: Oct. 27, 2026

(54) INJECTABLE MICRO-ANNEALED POROUS SCAFFOLD FOR ARTICULAR CARTILAGE REGENERATION

(71) Applicant: University of Virginia Patent Foundation, Charlottesville, VA (US)

(72) Inventors: Donald Richieri Griffin, Charlottesville, VA (US); Blaise N. Pfaff, Charlottesville, VA (US); Nicholas J. Cornell, Charlottesville, VA (US); Brent R. DeGeorge, Jr., Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 976 days.

(21) Appl. No.: 17/782,824

(22) PCT Filed: Dec. 7, 2020

(86) PCT No.: PCT/US2020/063597
§ 371 (c)(1),
(2) Date: Jun. 6, 2022

(87) PCT Pub. No.: WO2021/113812
PCT Pub. Date: Jun. 10, 2021

(65) Prior Publication Data

US 2023/0001055 A1 Jan. 5, 2023

Related U.S. Application Data

(60) Provisional application No. 62/944,750, filed on Dec. 6, 2019.

(51) Int. Cl.
*A61L 27/52* (2006.01)
*A61L 27/54* (2006.01)
*A61L 27/56* (2006.01)

(52) U.S. Cl.
CPC ............... *A61L 27/52* (2013.01); *A61L 27/54* (2013.01); *A61L 27/56* (2013.01);
(Continued)

(58) Field of Classification Search
None
See application file for complete search history.

(56) References Cited

U.S. PATENT DOCUMENTS

2016/0027928 A1 1/2016 Sato
2016/0279283 A1* 9/2016 Griffin .................... A61L 27/58
(Continued)

FOREIGN PATENT DOCUMENTS

WO WO 2016/011387 A1 1/2016
WO WO 2019/200390 A1 10/2019
WO WO 2021/113812 A1 6/2021

OTHER PUBLICATIONS

Griffin et al. (2015) Accelerated wound healing by injectable microporous gel scaffolds assembled from annealed building blocks. Nat Mater 14(7):737-744.
(Continued)

*Primary Examiner* — Dominic Lazaro
(74) *Attorney, Agent, or Firm* — JENKINS, TAYLOR & HUNT, P.A.

(57) ABSTRACT

Provided are compositions that can be employed for generating microporous gel systems. In some embodiments, the compositions include at least one sub-population of soft hydrogel microparticles with a Youngs modulus of less than 50 kPa and at least one sub-population of stiff hydrogel microparticles with a Young's modulus of greater than 90 kPa. Also provided are methods for generating the compositions, methods for treating bone and/or cartilage defects in subject using the disclosed compositions, methods for treat-
(Continued)

ing osteoarthritis using the disclosed compositions, and methods for providing orthopedic implants to subjects.

16 Claims, 4 Drawing Sheets

Specification includes a Sequence Listing.

(52) U.S. Cl.
CPC ..... *A61L 2300/236* (2013.01); *A61L 2300/25* (2013.01); *A61L 2400/06* (2013.01); *A61L 2430/02* (2013.01); *A61L 2430/06* (2013.01)

(56) References Cited

U.S. PATENT DOCUMENTS

| | | | |
|---|---|---|---|
| 2017/0196818 | A1 | 7/2017 | Shin et al. |
| 2017/0368224 | A1 | 12/2017 | Griffin et al. |
| 2018/0078671 | A1 | 3/2018 | Griffin et al. |
| 2019/0151497 | A1 | 5/2019 | Griffin et al. |
| 2019/0175230 | A1 | 6/2019 | D'Agostino et al. |
| 2019/0216979 | A1 | 7/2019 | De Laporte et al. |

OTHER PUBLICATIONS

International Preliminary Report on Patentability corresponding to PCT International Patent Application Serial No. PCT/US2020/0663597 dated Jun. 16, 2022.

Medved et al. (2013) Severe posttraumatic radiocarpal cartilage damage: first report of autologous chondrocyte implantation. Arch Orthop Trauma Surg 133(10):1469-1475.

Murphy et al. (2018) Medical Expenditures and Earnings Losses Among US Adults With Arthritis in 2013. Arthritis Care Res 70(6):869-876.

Nih, L., et al., "Injection of Microporous Annealing Particle (MAP) Hydrogels in the Stroke Cavity Reduces Gliosis and Inflammation and Promotes NPC Migration to the Lesion", Advanced Materials, 29(32):1606471, 2017, pp. 1-8.

Notice of Designated Office (DO) / Elected Office (EO) Acceptance Mailed, mailed on Mar. 29, 2023, in U.S. Appl. No. 17/782,824, 2 pages.

Notice of Publication, mailed on Jan. 5, 2023, in U.S. Appl. No. 17/782,824, 1 page.

Obert et al. (2013) "Rib Cartilage Graft for Posttraumatic or Degenerative Arthritis at Wrist Level: 10-Year Results.," J Wrist Surg.02(03):234-238.

Sideris et al. (2016) Particle Hydrogels Based on Hyaluronic Acid Building Blocks. ACS Biomater Sci Eng 2(11):2034-2041.

Toyras et al. (2001) Estimation of the Young's modulus of articular cartilage using an arthroscopic indentation instrument and ultrasonic measurement of tissue thickness. J Biomech 34(2):251-256.

Yang et al. (2018) Development of chondrocyte-seeded electrosprayed nanoparticles for repair of articular cartilage defects in rabbits. J Biomater Appl 32(6):800-812.

Engler et al. (2006) Matrix Elasticity Directs Stem Cell Lineage Specification. Cell 126:677-689.

Griffin et al. (2015) Accelerated wound healing by injectable microporous gel scaffolds assembled from annealed building blocks. Nature Materials 14(7):737-744.

International Preliminary Report on Patentability corresponding to PCT International Patent Application Serial No. PCT/US2020/063597 dated Jun. 16, 2022.

International Search Report and Written Opinion corresponding to PCT International Patent Application Serial No. PCT/US2020/063597 dated Mar. 18, 2021.

Mobasheri et al. (2014) Chondrocyte and mesenchymal stem cell-based therapies for cartilage repair in osteoarthritis and related orthopaedic conditions. Maturitas 78(3):188-198.

Nih et al. (2017) Injection of Microporous Annealing Particle (MAP) Hydrogels in the Stroke Cavity Reduces Gliosis and Inflammation and Promotes NPC Migration to the Lesion. Advanced Materials, 29(32):1606471.

Obert et al. (2013) Rib Cartilage Graft for Posttraumatic or Degenerative Arthritis at Wrist Level: 10-Year Results. Journal of Wrist Surgery 02(03):234-238.

Shin et al. (2014) Contractile Forces Sustain and Polarize Hematopoiesis from Stem and Progenitor Cells. Cell Stem Cell 14:81-93.

Yang et al. (2018) Development of chondrocyte-seeded electrosprayed nanoparticles for repair of articular cartilage defects in rabbits. Journal of Biomaterials Applications 32(6):800-812.

* cited by examiner

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Artificially synthesized cell adhesive peptide
```

-continued

<400> SEQUENCE: 1

```
Arg Gly Asp Ser Pro Gly Gly Cys
1               5
```

INJECTABLE MICRO-ANNEALED POROUS SCAFFOLD FOR ARTICULAR CARTILAGE REGENERATION

CROSS REFERENCE TO RELATED APPLICATION

The presently disclosed subject matter claims the benefit of U.S. Provisional Patent Application Ser. No. 62/944,750 filed Dec. 6, 2019, the disclosure of which is incorporated herein by reference in its entirety.

TECHNICAL FIELD

The presently disclosed subject matter relates in some embodiments to compositions and methods for enhancing both articular cartilage and subchondral bone biointegration and chondrogenic regeneration. In some embodiments, the presently disclosed subject matter relates to a composition comprising, consisting essentially of, or consisting of soft hydrogel microparticles and stiff hydrogel microparticles and methods for generating microporous gel systems that comprise the same.

BACKGROUND

Arthritis of the hand and wrist is a chronic, disabling condition that affects roughly 4 million Americans annually with an estimated annual cost in terms of healthcare expenditure and decreased productivity exceeding $300 billion (Murphy et al., 2013). Osteoarthritis (OA) is characterized by progressive, irreparable loss of articular cartilage due to its limited intrinsic repair capacity because of its relative lack of blood supply and low cellular proliferation rate. Therefore, current treatment strategies are focused on replenishing the lost articular cartilage. Osteochondral grafting and autologous chondrocyte implantation have been employed to replace degenerated or damaged cartilage (Medved et al., 2013; Obert et al., 2013). These methods have shown limited long term efficacy and do not significantly modify OA symptoms (Mobasheri et al., 2014). Many hypothesize these methods of chondrocyte transplantation failed in part due to the lack of a nourishing environment to promote chondrogenesis (Yang et al., 2018). Additionally, transplantation of cartilage is an open, invasive procedure.

A major obstacle in the management of OA remains the inability to effectively restore articular cartilage, restricting the options for patients to continued non-operative management, joint replacement, or ablation in the form of arthroplasty or arthrodesis. Tissue-engineered cartilage replacements represent an innovative approach to promote the development of functional articular cartilage and potentially avoid total joint replacement. However, the optimum mechanical and biochemical properties of the substrate material have yet to be defined, and leakage of the substrate, inadequate integration of host tissue, and insufficient structural support are common problems in tissue-engineered approaches (Armiento et al., 2018).

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter relates to a soft-stiff hybrid hydrogel particle composition for use as an injectable hard tissue regenerative scaffold. In some embodiments, the presently disclosed subject matter relates to a MAP scaffold specialized for long-term treatment of cartilage and/or bone.

More particularly, in some embodiments the presently disclosed subject matter relates to compositions comprising at least one sub-population of soft hydrogel microparticles with a Young's modulus of less than 50 kPa and at least one sub-population of stiff hydrogel microparticles with a Young's modulus of greater than 90 kPa. In some embodiments, the average diameter of the soft hydrogel microparticles, the stiff hydrogel microparticles, or both is between about 1 and 1000 μm.

In some embodiments of the presently disclosed compositions, the soft hydrogel microparticles, the stiff hydrogel microparticles, or both are spherical or substantially spherical. In some embodiments, the compositions further comprise an annealing initiator, optionally wherein the annealing initiator is selected from the group consisting of a photoinitiator (optionally Eosin-Y or lithium phenyl-(2,4,6-trimethyl benzoyl) phosphinate; LAP), a small molecule crosslinker, a soluble crosslinker, a heat-activated crosslinker, a spontaneous radical generating crosslinker combination (optionally ammonium persulfate with tetramethylethylenediamine), and an enzymatic crosslinker (optionally Factor XIII), wherein the annealing initiator facilitates annealing of the at least one soft hydrogel and the at least one stiff hydrogel to form a microporous annealed particle (MAP) scaffold. In some embodiments, both the at least one sub-population of soft hydrogel microparticles and at least one sub-population of stiff hydrogel microparticles comprise one or more methacrylamide functionalities that permit inter-microparticle surface chemical annealing of at least one soft hydrogel microparticle and at least one stiff hydrogel microparticle to create a microporous annealed particle (MAP) scaffold.

In some embodiments of the presently disclosed compositions, the volume of the at least one soft hydrogel microparticle sub-population present in the composition is in a ratio of 1:10-1:3 with respect to the volume of the at least one stiff hydrogel microparticle sub-population in the composition.

In some embodiments of the presently disclosed compositions, the at least one soft hydrogel microparticle sub-population, the at least one stiff hydrogel microparticle sub-population, or both comprise a polyethylene glycol (PEG), optionally a PEG with an average molecular weight of 10 kiloDaltons (kDa).

In some embodiments of the presently disclosed compositions, the composition further comprises one or more additional active agents, wherein the one or more additional active agents are optionally selected from the group consisting of a cell adhesive peptide, optionally an RGD-containing cell adhesive peptide, further optionally a peptide comprising, consisting essentially of, or consisting of the amino acid sequence RGDSPGGC (SEQ ID NO: 1); chondroitin sulfate (CS), optionally thiolated CS, heparin, and combinations thereof.

In some embodiments, the presently disclosed subject matter also relates to methods for generating a microporous gel system. In some embodiments, the methods comprise combining at least one soft hydrogel microparticle sub-population with a Young's modulus of less than 50 kPa and at least one stiff hydrogel microparticle sub-population with a Young's modulus of greater than 90 kPa to create a mixture; and annealing the at least one soft hydrogel microparticle sub-population and the at least one stiff hydrogel microparticle sub-population in the mixture, whereby a microporous gel system is generated. In some embodiments, the annealing is accomplished with an annealing initiator, optionally wherein the annealing initiator is selected from the group consisting of a photoinitiator (optionally Eosin-Y or lithium phenyl-(2,4,6-trimethyl benzoyl) phosphinate; LAP), a small molecule crosslinker, a soluble crosslinker, a heat-activated crosslinker, a spontaneous radical generating crosslinker combination (optionally ammonium persulfate with tetramethylethylenediamine), and an enzymatic crosslinker (optionally Factor XIII). In some embodiments, both the at least one soft hydrogel microparticle sub-population and the at least one stiff hydrogel microparticle sub-population comprise one or more methacrylamide functionalities that permit crosslinking of the at least one soft hydrogel microparticle sub-population and the at least one stiff hydrogel microparticle sub-population in order to generate the microporous gel system. In some embodiments, the methacrylamide functionalities are provided by a four-arm PEG molecule, wherein the four-arm PEG molecule comprises about one arm of maleimide to facilitate attachment to a chemical network backbone of the at least one soft hydrogel microparticle sub-population and the at least one stiff hydrogel microparticle sub-population, and about three arms of methacrylamide to promote polymerization and/or annealing of the microporous gel system. In some embodiments, the at least one soft hydrogel microparticle sub-population is present in the mixture in a mass ratio of 1:10-1:3 to the at least one stiff hydrogel microparticle sub-population. In some embodiments, the at least one soft hydrogel microparticle sub-population, the at least one stiff hydrogel microparticle sub-population, or both comprise a polyethylene glycol, optionally a PEG with an average molecular weight of 10 kiloDaltons (kDa). In some embodiments, the at least one soft hydrogel, the at least one stiff hydrogel, or both further comprise one or more additional active agents, wherein the one or more additional active agents are optionally selected from the group consisting of a cell adhesive peptide, optionally an RGD-containing cell adhesive peptide, further optionally a peptide comprising, consisting essentially of, or consisting of the amino acid sequence RGDSPGGC (SEQ ID NO: 1); chondroitin sulfate (CS), optionally thiolated CS, heparin, and combinations thereof.

In some embodiments, the presently disclosed subject matter also relates to methods for treating bone and/or cartilage defects in subjects. In some embodiments, the methods comprise introducing into a bone and/or cartilage defect in a subject a composition as disclosed herein in an amount sufficient to substantially or completely fill the bone and/or cartilage defect, and annealing the at least one soft hydrogel and the at least one stiff hydrogel present in the composition such that a microporous annealed particle (MAP) scaffold is produced in the bone and/or cartilage defect. In some embodiments, the MAP scaffold persists in the bone and/or cartilage defect for a time sufficient for host cell migration into the bone and/or cartilage defect to occur. In some embodiments, the bone and/or cartilage defect is present in a knee, elbow, or wrist of the subject. In some embodiments, the bone and/or cartilage defect is associated with osteoarthritis in the subject and/or is created in the subject in order to provide a space into which a composition of the presently disclosed subject matter can be introduced to thereby treat the osteoarthritis. In some embodiments, the composition of the presently disclosed subject matter is injected into the bone and/or cartilage defect in the subject, optionally wherein the injection is carried out arthroscopically. In some embodiments, the presently disclosed composition induces glycosoaminoglycan expression within the MAP scaffold in the subject. In some embodiments, the presently disclosed composition that is present in the bone and/or cartilage defect induces little or no inflammatory response to the MAP scaffold in the subject.

In some embodiments of the presently disclosed methods, the annealing comprises exposing a composition of the presently disclosed subject matter that is present in the bone and/or cartilage defect to light of an appropriate wavelength, intensity, and duration to produce the MAP scaffold.

In some embodiments, the presently disclosed subject matter also relates to methods for treating osteoarthritis in subjects. In some embodiments, the methods comprise introducing into a bone and/or cartilage space associated with osteoarthritis or created in a subject to treat the osteoarthritis a composition of the presently disclosed subject matter in an amount sufficient to substantially or completely fill the bone and/or cartilage space, and annealing the at least one soft hydrogel and the at least one stiff hydrogel present in the composition of the presently disclosed subject matter such that a microporous annealed particle (MAP) scaffold is produced in the bone and/or cartilage space. In some embodiments, the MAP scaffold persists in the bone and/or cartilage space for a time sufficient for host cell migration into the bone and/or cartilage space to occur. In some embodiments, the bone and/or cartilage space is present in a knee, elbow, or wrist of the subject. In some embodiments, the composition of the presently disclosed subject matter is injected into the bone and/or cartilage space in the subject, optionally wherein the injection is carried out arthroscopically. In some embodiments, the composition of the presently disclosed subject matter induces glycosoaminoglycan expression within the MAP scaffold in the subject. In some embodiments, the composition of the presently disclosed subject matter that is present in the bone and/or cartilage space induces little or no inflammatory response to the MAP scaffold in the subject. In some embodiments, the annealing comprises exposing the composition introduced into the bone and/or cartilage space to light of an appropriate wavelength, intensity, and duration to produce the MAP scaffold in the bone and/or cartilage space.

In some embodiments, the presently disclosed subject matter also relates to methods for providing implants to subjects. In some embodiments, the methods comprise introducing into a bone and/or cartilage space associated with a bone and/or cartilage defect or created in the subject to treat the bone and/or cartilage defect an implant appropriate for the bone and/or cartilage defect and a composition of the presently disclosed subject matter and annealing the at least one soft hydrogel and the at least one stiff hydrogel present in the composition such that a microporous annealed particle (MAP) scaffold is produced in the bone and/or cartilage space such that apposition of the implant to the tissue surrounding the bone and/or cartilage space is enhanced relative to apposition of the implant to the tissue surrounding the bone and/or cartilage space in the absence of the MAP. In some embodiments, the MAP scaffold persists in the bone and/or cartilage space for a time sufficient for host cell migration into the bone and/or cartilage space to occur. In some embodiments, the bone and/or cartilage space is present in a knee, elbow, or wrist of the subject. In some embodiments, the composition of the presently disclosed subject matter is injected into the bone and/or cartilage space in the subject, optionally wherein the injection is carried out arthroscopically or as part of open surgery. In some embodiments, the composition induces glycosoaminoglycan expression within the MAP scaffold in the subject. In some embodiments, the composition of the presently disclosed subject matter present in the bone and/or cartilage space induces little or no inflammatory response to the MAP scaffold in the subject. In some embodiments, the annealing comprises exposing the composition present in the bone and/or cartilage space to light of an appropriate wavelength, intensity, and duration to produce the MAP scaffold in the bone and/or cartilage space.

Accordingly, it is an object of the presently disclosed subject matter to provide compositions and methods for enhancing articular cartilage regeneration. An object of the presently disclosed subject matter having been stated hereinabove, and which is achieved in whole or in part by the presently disclosed subject matter, other objects will become evident as the description proceeds hereinbelow.

BRIEF DESCRIPTION OF THE FIGURES

FIG. 1A is a photograph of an exposed femoral head with a 2.5-mm diameter 2.5-mm defect drilled at the center of the trochlea. FIG. 1B is a photograph showing a MAP gel of the presently disclosed subject matter being applied to the defect. FIG. 1C is a photograph showing the exemplary MAP gel being annealed with 505 nm green light. LFC=lateral femoral condyle; MFC=medial femoral condyle; TG=trochlear groove. Scale bar in FIG. 1A is 5 mm.

FIG. 2A is a photograph of a saline-treated knee, which demonstrates evidence of significant scar formation around the defect with a more collapsed surface (arrow). FIG. 2B is a photograph of a knee treated with an exemplary MAP gel of the presently disclosed subject matter, showing how the MAP gel provided a scaffold that allowed for a smooth surface of the defect with minimal adjacent scar tissue. The scale bars in FIGS. 2A and 2B both represent 2 mm.

FIG. 3A is a saline-treated defect at 8 weeks showing that the defect was collapsed and filled with fibrotic scar tissue (arrow). FIG. 3B is a MAP gel-treated defect at 4 weeks post-operatively showing that the MAP gel maintained its position within the defect and native tissue had begun to migrate over the smooth surface. Minimal immune response was evidenced by the lack of polymorphonuclear cells. FIG. 3C is a MAP gel-treated defect that, by 8 weeks post-operatively, showed that the MAP gel was still within the defect with evidence of significant tissue ingrowth within and on the surface of the scaffold. Scale bars in each Figure represent 1 mm.

In FIG. 4A, the defect created in a saline-treated knee resulted in a disruption of the cartilage as seen with the lack of red GAP staining at the wound surface. FIG. 4B is a section of a MAP-treated defect showing evidence of the MAP gel supporting tissue migration over the surface that also contained GAG. The inset below shows a higher magnification of the wound surface with red staining even at the surface. FIG. 4C shows a MAP gel-treated defect at 8 weeks. Scale bars represent 1 mm in each case.

DETAILED DESCRIPTION

Figure 1A:
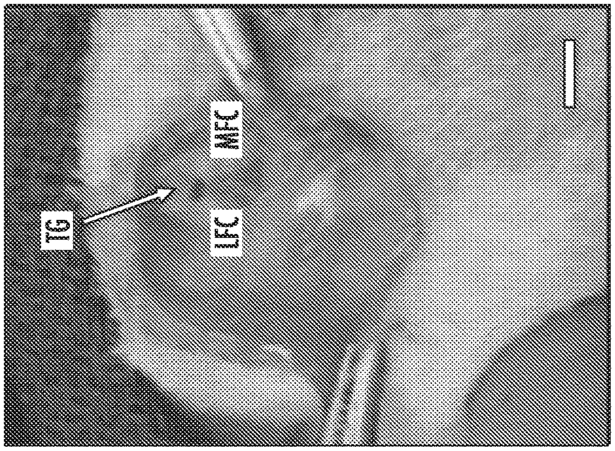
FIGS. 1A-1C depict an exemplary method for employing the MAP gels of the presently disclosed subject matter.

Disclosed herein is the implementation of a relatively new class of injectable biomaterial utilizing micro-gel building blocks to assemble a microporous annealed particle (MAP) scaffold in response to a light stimulus. Once acted upon by an annealing initiator such as but not limited to stimulation by light, the injected microspheres are chemically annealed to one another (and to surrounding tissue) through permanent covalent bonds to form a solid and hyper-porous scaffold to support tissue ingrowth (Griffin et al., 2015). This porous biomaterial allows for an accelerated window of tissue-biomaterial integration and the flowable nature makes the MAP gel an ideal candidate for arthroscopic procedures, for example in the treatment of wrist osteoarthritis (OA). Each microparticle is created using extremely tunable synthetic hydrogel chemistry and can be engineered to match the mechanical and chemical needs of the environment. In some embodiments, microparticle stiffness and mechanisms of degradation (e.g., the removal of a protease-sensitive peptide linker) were modified to produce a MAP scaffold specialized for long-term treatment of cartilage, bone, or other anatomical structures.

I. Abbreviations

BMP-2: bone morphogenetic protein 2
BMP-4: bone morphogenetic protein 4
BMP-7: bone morphogenetic protein 7
CAT: computerized axial tomography
CS: chondroitin sulfate
CT: computerized tomography
D: Diameter
DMTMM: 4-(4,6-Dimethoxy-1,3,5-triazin-2-yl)-4-methylmorpholinium chloride
GAG: glycosaminoglycan
H&E: hematoxylin and eosin
HA: hyaluronic acid
kDa: kiloDaltons
kPa: kilopascal
LAP: lithium phenyl-(2,4,6-trimethyl benzoyl) phosphinate
LED: light emitting diode
LFC: lateral femoral condyle
MAP: microporous annealed particle
MFC: medial femoral condyle
MSC mesenchymal stem cell
MWCO: molecular weight cut-off
OA: osteoarthritis
OCD: osteochondral defect
PBS: phosphate buffered saline
PDGF: platelet-derived growth factor
PDI: polydispersity index
PEG: polyethylene glycol
PEG-MAL: poly(ethylene glycol) maleimide
PEG-$NH_2$: poly(ethylene glycol) amine
PEG-SH: poly(ethylene glycol) thiol
PET: positron emission tomography
PLGA: poly(lactic-co-glycolic acid)
TEA: Triethylamine
TFA: trifluoroacetic acid
TG: trochlear groove
TGF-β: transforming growth factor beta
TNBSA: 2,4,6-trinitrobenzene sulfonic acid II. Definitions The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms “a”, “an”, and “the” refer to “one or more” when used in this application, including the claims. Thus, for example, reference to “a cell” includes a plurality of such cells, and so forth.

Unless otherwise indicated, all numbers expressing quantities of ingredients, reaction conditions, and so forth used in the specification and claims are to be understood as being modified in all instances by the term “about”. Accordingly, unless indicated to the contrary, the numerical parameters set forth in this specification and attached claims are approximations that can vary depending upon the desired properties sought to be obtained by the presently disclosed subject matter.

As used herein, the term “about,” when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term “comprising”, which is synonymous with “including” “containing” or “characterized by” is inclusive or open-ended and does not exclude additional, unrecited elements or method steps. “Comprising” is a term of art used in claim language which means that the named elements are essential, but other elements can be added and still form a construct within the scope of the claim.

As used herein, the phrase “consisting of” excludes any element, step, or ingredient not specified in the claim. When the phrase “consists of” appears in a clause of the body of a claim, rather than immediately following the preamble, it limits only the element set forth in that clause; other elements are not excluded from the claim as a whole.

As used herein, the phrase “consisting essentially of” limits the scope of a claim to the specified materials or steps, plus those that do not materially affect the basic and novel characteristic(s) of the claimed subject matter.

With respect to the terms “comprising”, “consisting of”, and “consisting essentially of”, where one of these three terms is used herein, the presently disclosed and claimed subject matter can include the use of either of the other two terms.

As used herein, the term “and/or” when used in the context of a listing of entities, refers to the entities being present singly or in combination. Thus, for example, the phrase “A, B, C, and/or D” includes A, B, C, and D individually, but also includes any and all combinations and subcombinations of A, B, C, and D.

III. Compositions of the Presently Disclosed Subject Matter

In some embodiments, the presently disclosed subject matter provides compositions that can be used to generate microporous annealed particle (MAP) scaffolds and/or microporous gel systems. In some embodiments, the MAP scaffolds and/or microporous gel systems can be used to treat bone and/or cartilage defects, diseases, disorders, or conditions such as but not limited to osteoarthritis.

In some embodiments, the compositions of the presently disclosed subject matter comprise at least two components: a first component comprising at least one sub-population of soft hydrogel microparticles and a second component comprising at least one sub-population of stiff hydrogel microparticles. As used herein, the term “soft hydrogel” refers to a hydrogel having a Young’s modulus of less than 50 kPa. As used herein, the term “stiff hydrogel” refers to a hydrogel with a Young’s modulus of greater than 90 kPa. Methods for measuring the Young’s modulus of a hydrogel are known in the art (see e.g., U.S. Pat. No. 9,447,381, incorporated herein by reference in its entirety) and are described herein, such as in the EXAMPLES.

The relative amounts of the at least one soft hydrogel microparticle sub-population and the at least one stiff hydrogel microparticle sub-population can vary in the composition, depending in some embodiments on the end use planned for the compositions. By way of example and not limitation, in some embodiments the volume of the at least one soft hydrogel microparticle sub-population present in the composition is in a ratio of 1:10-1:3 with respect to the volume of the at least one stiff hydrogel microparticle sub-population in the composition.

In some embodiments, the soft hydrogel and the stiff hydrogel are combined, and the microparticles that make up the hydrogels are annealed (in some embodiments, crosslinked) to form the MAP scaffolds and/or microporous gel systems. While not wishing to be limited by any particular theory of operation, the mixing soft and stiff microparticles permits the annealing event that bonds the microparticles together (and thus the construction of the scaffold) to happen. Importantly, if only stiff microparticles (which match the mechanical environment and needed mechanical signaling for these tissues) alone are employed, it has been determined that they do not anneal to one another effectively. This might be due to them not deforming adequately to provide a sufficient surface area for formation of linkages between microparticles. Additionally, if only soft microparticles are employed, they will anneal but the desired mechanical signaling environment needed for matching cartilage and promoting chondrogenesis is not generated.

Accordingly, the use of both soft and stiff microparticles together has been found to provide the unexpected benefit that both the desired scaffolding as well as the desired mechanical signaling environment can be generated.

Thus, in some embodiments the composition further comprises an annealing initiator to facilitate annealing/crosslinking of the microparticles. In some embodiments, the annealing initiator is selected from the group consisting of a photoinitiator (which can in some embodiments be Eosin-Y and/or lithium phenyl-(2,4,6-trimethyl benzoyl) phosphinate; LAP), although other crosslinkers can be employed based on the functionality employed to effectuate the crosslinking. By way of example and not limitation, small molecule crosslinkers, soluble crosslinkers, heat-activated crosslinkers, spontaneous radical generating crosslinker combinations (including but not limited to ammonium persulfate and tetramethylethylenediamine), and enzymatic crosslinkers (such as but not limited to Factor XIII) can be employed, provided that the annealing initiator facilitates annealing of the at least one soft hydrogel and the at least one stiff hydrogel to form a microporous annealed particle (MAP) scaffold.

In a non-limiting example, in some embodiments both the at least one sub-population of soft hydrogel microparticles and at least one sub-population of stiff hydrogel microparticles comprise one or more methacrylamide functionalities that permit inter-microparticle surface chemical annealing of at least one soft hydrogel microparticle and at least one stiff hydrogel microparticle to create a microporous annealed particle (MAP) scaffold.

The microparticles employed can have any backbone structure, provided that the soft hydrogel is a hydrogel having a Young's modulus of less than 50 kPa and the stiff hydrogel is a hydrogel with a Young's modulus of greater than 90 kPa. Exemplary materials upon which the hydrogels can be based are disclosed in U.S. Patent Application Publication Nos. 2016/0279283, 2017/0368224, 2018/0078671, and 2019/0151497, each of which is incorporated herein by reference in its entirety. By way of example and not limitation, the hydrogel microparticles can be made from a hydrophilic polymer, amphiphilic polymer, synthetic or natural polymer (e.g., poly(ethylene glycol) (PEG), poly (propylene glycol), poly(hydroxyethylmethacrylate), hyaluronic acid (HA), gelatin, fibrin, chitosan, heparin, heparan, and synthetic versions of HA, gelatin, fibrin, chitosan, heparin, or heparan). In some embodiments, the hydrogel microparticles are made from any natural (e.g., modified HA) or synthetic polymer (e.g., PEG) capable of forming a hydrogel. In some embodiments, a polymeric network and/or any other support network capable of forming a solid hydrogel construct may be used. Suitable support materials for most tissue engineering/regenerative medicine applications are generally biocompatible and preferably biodegradable. Examples of suitable biocompatible and biodegradable supports include: natural polymeric carbohydrates and their synthetically modified, crosslinked, or substituted derivatives, such as gelatin, agar, agarose, crosslinked alginic acid, chitin, substituted and cross-linked guar gums, cellulose esters, especially with nitrous acids and carboxylic acids, mixed cellulose esters, and cellulose ethers; natural polymers containing nitrogen, such as proteins and derivatives, including cross-linked or modified gelatins, and keratins; vinyl polymers such as poly(ethyleneglycol)acrylate/methacrylate/vinyl sulfone/maleimide/norbornene/allyl, polyacrylamides, polymethacrylates, copolymers and terpolymers of the above polycondensates, such as polyesters, polyamides, and other polymers, such as polyurethanes; and mixtures or copolymers of the above classes, such as graft copolymers obtained by initializing polymerization of synthetic polymers on a preexisting natural polymer. A variety of biocompatible and biodegradable polymers are available for use in therapeutic applications; examples include: polycaprolactone, polyglycolide, polylactide, poly(lactic-co-glycolic acid) (PLGA), and poly-3-hydroxybutyrate.

In some embodiments, the at least one soft hydrogel microparticle sub-population, the at least one stiff hydrogel microparticle sub-population, or both comprise a polyethylene glycol (PEG), optionally a PEG with an average molecular weight of 10 kiloDaltons (kDa). In some embodiments, the hydrogels are based on a four-arm PEG with about one arm of maleimide (which allows attachment to hydrogel chemical network backbone) and about three arms of methacrylamide to promote the polymerization/annealing reaction.

In any of the embodiments of the presently disclosed subject matter, the degree to which the annealing/crosslinking occurs can be adjusted to create more or less crosslinking via adjustment of the parameters under which the annealing/crosslinking occurs.

In addition to the at least one soft hydrogel microparticle sub-population, the at least one stiff hydrogel microparticle sub-population, and the annealing initiator(s), the compositions of the presently disclosed subject matter can also include one or more additional active agents. By way of example and not limitation, the one or more additional active agents can be selected from the group consisting of a cell adhesive peptide, optionally an RGD-containing cell adhesive peptide, further optionally a peptide comprising, consisting essentially of, or consisting of the amino acid sequence RGDSPGGC (SEQ ID NO: 1); chondroitin sulfate (CS), optionally thiolated CS, heparin, and combinations thereof.

For example, in some embodiments the compositions further comprise mesenchymal stem cells (MSCs), chondrocyte progenitor cells, chondrocyte primary cells as targets for cartilage, MSCs and/or osteocytes as targets for bone), one or more growth factors, including but not limited to BMP-2, BMP-4, BMP-7, PDGF, TGF-β, and combinations thereof. Heparin, chondroitin sulfate, and hyaluronic acid are also examples of bioactive polymers that can be employed in the compositions of the presently disclosed subject matter.

IV. Methods for Making the Presently Disclosed Compositions

In some embodiments, the presently disclosed subject matter also pertains to methods for generating microporous gel systems. General approaches to generating microporous gel systems are disclosed in U.S. Patent Application Publication Nos. 2016/0279283, 2017/0368224, 2018/0078671, and 2019/0151497, each of which is incorporated herein by reference in its entirety. However, the basic strategies disclosed in these patent application publications were found to be less applicable for use in treating bone and/or cartilage defects, and thus new strategies were developed as disclosed herein wherein at least one soft hydrogel microparticle sub-population and at least one stiff hydrogel microparticle sub-population are combined in order to create microporous gel systems that are flowable prior to annealing for ease of introduction into bone and/or cartilage spaces, and once annealed can provide a stable structure that is retained in the bone and/or cartilage spaces and in some embodiments provide a scaffold onto which a subject's cells can migrate and/or adhere in order to treating and/or prevent bone and/or cartilage defects. It was determined that the use of both soft and stiff hydrogel microparticle sub-populations in appropriate ratios could provide the desired characteristics.

Thus, in some embodiments the methods comprise combining at least one soft hydrogel microparticle sub-population and at least one stiff hydrogel microparticle sub-population to create a mixture; and annealing the at least one soft hydrogel microparticle sub-population and the at least one stiff hydrogel microparticle sub-population in the mixture, whereby a microporous gel system is generated. As used herein, the phrase "soft hydrogel microparticle sub-population" refers to a hydrogel microparticle sub-population wherein the microparticles are characterized by a Young's modulus of less than 50 kPa. Exemplary Young's moduli for a soft hydrogel microparticle sub-population include less than about 10 kPa, in some embodiments less than about 15 kPa, in some embodiments less than about 20 kPa, in some embodiments less than about 25 kPa, in some embodiments less than about 30 kPa, in some embodiments less than about 35 kPa, in some embodiments less than about 40 kPa, in some embodiments less than about 45 kPa, and in some embodiments less than about 50 kPa. As used herein, the phrase "stiff hydrogel microparticle sub-population" refers to a hydrogel microparticle sub-population wherein the microparticles are characterized by a Young's modulus of greater than about 90 kPa. Exemplary Young's moduli for a stiff hydrogel microparticle sub-population include greater than about 90 kPa, in some embodiments greater than about 95 kPa, and in some embodiments greater than about 100 kPa.

The ratio of the soft hydrogel microparticle sub-population to the stiff hydrogel microparticle sub-population can also influence the performance of the microporous gel system generated. In some embodiments, the at least one soft hydrogel microparticle sub-population is present in the mixture in a mass ratio of 1:10-1:3 to the at least one stiff hydrogel microparticle sub-population.

In order to produce the microporous gel system, the desired amounts of soft and stiff hydrogel microparticle sub-populations and combined and annealed. Any method for annealing the soft and stiff hydrogel microparticle sub-populations can be employed. Exemplary annealing strategies are also disclosed in U.S. Patent Application Publication Nos. 2016/0279283, 2017/0368224, 2018/0078671, and 2019/0151497. By way of example and not limitation, in some embodiments the annealing is accomplished with an annealing initiator, optionally wherein the annealing initiator is selected from the group consisting of a photoinitiator (optionally Eosin-Y and/or lithium phenyl-(2,4,6-trimethyl benzoyl) phosphinate; LAP), a small molecule crosslinker, a soluble crosslinker, a heat-activated crosslinker, a spontaneous radical generating crosslinker combination (optionally ammonium persulfate with tetramethylethylenediamine), and an enzymatic crosslinker (optionally Factor XIII).

In some embodiments, the annealing can depend on the functionalities present in the soft and stiff hydrogel microparticle sub-populations. In a non-limiting example of the presently disclosed subject matter, in some embodiments both the at least one soft hydrogel microparticle sub-population and the at least one stiff hydrogel microparticle sub-population comprise one or more methacrylamide functionalities that permit crosslinking of the at least one soft hydrogel microparticle sub-population and the at least one stiff hydrogel microparticle sub-population in order to generate the microporous gel system.

The at least one soft hydrogel microparticle sub-population and the at least one stiff hydrogel microparticle sub-population can be based on any scaffold structure, including but not limited to PEG, hyaluronic acid, and/or collagen. PEG, hyaluronic acid, collagen, or other scaffold structures can be employed as desired, provided that the at least one soft hydrogel microparticle sub-population and the at least one soft hydrogel microparticle sub-population comprises microparticles characterized by a Young's modulus of less than about 50 kPa and the at least one stiff hydrogel microparticle sub-population comprises microparticles characterized by a Young's modulus of greater than about 90 kPa.

In some embodiments, the at least one soft hydrogel microparticle sub-population, the at least one stiff hydrogel microparticle sub-population, or both comprise a polyethylene glycol, optionally a PEG with an average molecular weight of 10 kiloDaltons (kDa).

In some embodiments, the methacrylamide functionalities are provided by a four-arm PEG molecule, wherein the four-arm PEG molecule comprises about one arm of maleimide to facilitate attachment to a chemical network backbone of the at least one soft hydrogel microparticle sub-population and the at least one stiff hydrogel microparticle sub-population, and about three arms of methacrylamide to promote polymerization and/or annealing of the microporous gel system.

In some embodiments, additional active agents, such as but not limited to cell attractants, cell adhesion enhancers, and/or other bioactive molecules can be included in the at least one soft hydrogel, the at least one stiff hydrogel, or both, as desired. Thus, in some embodiments the at least one soft hydrogel, the at least one stiff hydrogel, or both can further comprise one or more additional active agents, wherein the one or more additional active agents are optionally selected from the group consisting of a cell adhesive peptide, optionally an RGD-containing cell adhesive peptide, further optionally a peptide comprising, consisting essentially of, or consisting of the amino acid sequence RGDSPGGC (SEQ ID NO: 1). Other actives that can be employed include, but are not limited to chondroitin sulfate (CS), optionally thiolated CS, heparin, and combinations thereof.

V. Treatment and/or Prevention Methods for Using the Presently Disclosed Compositions In some embodiments, the presently disclosed subject matter also relates to methods for treating and/or preventing bone and/or cartilage defects, disorders, and/or conditions using the compositions of the presently disclosed subject matter. Thus, in some embodiments the presently disclosed subject matter pertains to methods for treating a bone and/or cartilage defects, disorders, and/or conditions in a subject in need thereof, in which the methods comprise introducing into a bone and/or cartilage defect a composition as disclosed herein in an amount and via a route sufficient to substantially or completely fill the bone and/or cartilage defect, and annealing the at least one soft hydrogel and the at least one stiff hydrogel present in the composition such that a microporous annealed particle (MAP) scaffold is produced in the bone and/or cartilage defect in order to treat and/or prevent a bone and/or cartilage defect, disorder, and/or condition in the subject. In some embodiments, the MAP scaffold persists in the bone and/or cartilage defect for a time sufficient for host cell migration into the bone and/or cartilage defect to occur. In some embodiments, the bone and/or cartilage defect is present in a knee, elbow, or wrist of the subject. In some embodiments, the presently disclosed composition is injected into the bone and/or cartilage defect in the subject, optionally wherein the injection is carried out arthroscopically. In some embodiments, the presently disclosed composition induces glycosoaminoglycan expression within the MAP scaffold in the subject. In some embodiments, the presently disclosed composition introduced into the bone and/or cartilage defect induces little or no inflammatory response to the MAP scaffold in the subject.

Once introduced into a bone and/or cartilage defect, the MAP scaffold is generated by annealing the at least one soft hydrogel and the at least one stiff hydrogel present in the composition. Strategies for annealing the at least one soft hydrogel and the at least one stiff hydrogel are disclosed herein. In those embodiments, the annealing strategy employed can take into account the fact that the annealing occurs in vivo in the body of a subject, and thus should employ annealing enhancers that are pharmaceutically acceptable for use in vivo, including but not limited to in vivo in a human. Thus, in some embodiments the annealing strategy employs a light-sensitive annealing initiator such as but not limited to Eosin-Y and/or lithium phenyl-(2,4,6-trimethyl benzoyl) phosphinate (LAP) and exposure of the introduced composition of the presently disclosed subject matter to light of an appropriate wavelength, intensity, and duration to produce the MAP scaffold.

In some embodiments, of the presently disclosed methods, the bone and/or cartilage defect is associated with osteoarthritis in the subject or is created in the subject in order to provide a space into which a composition of the presently disclosed subject matter can be introduced to treat the osteoarthritis. As such, in some embodiments the presently disclosed subject matter pertains to methods comprising introducing into a bone and/or cartilage space associated with osteoarthritis or created in the subject to treat the osteoarthritis a composition of the presently disclosed subject matter in an amount sufficient to substantially or completely fill the bone and/or cartilage space, and annealing the at least one soft hydrogel and the at least one stiff hydrogel present in the composition such that a microporous annealed particle (MAP) scaffold is produced in the bone and/or cartilage space. In some embodiments, the bone and/or cartilage space for a time sufficient for host cell migration into the bone and/or cartilage space to occur. In some embodiments, the bone and/or cartilage space is present in a knee, elbow, or wrist of the subject. In some embodiments, the presently disclosed composition is injected into the bone and/or cartilage space in the subject, optionally wherein the injection is carried out arthroscopically. In some embodiments, a composition of the presently disclosed subject matter induces glycosoaminoglycan expression within the MAP scaffold in the subject. In some embodiments, the presence of the composition in the bone and/or cartilage space induces little or no inflammatory response to the MAP scaffold in the subject.

In the treatment and/or prevention methods disclosed herein, it can be of interest for the microporous gel systems to be introduced into a bone and/or cartilage defect in order to provide a foundation for remodeling of the defect by attracting migration of cells to the defect. Thus, in some embodiments mesenchymal stem cells (MSCs), chondrocyte progenitor cells, and/or chondrocyte primary cells can be included with at least one soft hydrogel, the at least one stiff hydrogel, or both, as desired, for cartilage defects, and MSCs and/or osteocytes can be included in the at least one soft hydrogel, the at least one stiff hydrogel, or both, as desired, for bone defects. One or more growth factors can also be included in the at least one stiff hydrogel, or both. Exemplary non-limiting growth factors that can be employed, as desired, include BMP-2, BMP-4, BMP-7, PDGF, and TGF-β, either alone or in any combination.

In some embodiments, a detectable moiety is included in the at least one soft hydrogel, the at least one stiff hydrogel, or both, to facilitate visualization of the composition in the bone and/or cartilage defect before, during, and/or subsequent to annealing. In some embodiments, the detectable moiety is one that can be detected by current medical visualization techniques including, but not limited to ultrasound, CT scanning, CAT scanning, PET scanning, etc. In some embodiments, the detectable moiety comprises a fluorescent functionality, which in some embodiments can be an ALEXA FLUOR® molecule.

In some embodiments, the compositions of the presently disclosed subject matter are employed as part of an implant surgery, such as an orthopedic implant surgery. In some embodiments, the compositions of the presently disclosed subject matter can be employed to fill the void space between the implant and the tissue in order to provide enhanced apposition of the between the implant and the tissue. In such embodiments, the compositions of the presently disclosed subject matter can be employed in conjunction with or instead of bone cement. The compositions of the presently disclosed subject matter can be employed in conjunction with any implant, including any orthopedic implant, including but not limited to implants designed for use in a skeletal joint, including, but not limited to, joints of the hip, knee, shoulder, spine, elbow, wrist, ankle, jaw, and digits.

V.A. Subjects

In some embodiments, the presently disclosed compositions are introduced into subjects in order to treat or prevent the development of a disease, disorder, condition, or a symptom thereof in the subject. The subject treated in the presently disclosed subject matter is desirably a human subject, although it is to be understood that the principles of the disclosed subject matter indicate that the compositions and methods are effective with respect to invertebrate and to all vertebrate species, including mammals, which are intended to be included in the term "subject." Moreover, a mammal is understood to include any mammalian species in which treatment of bone and/or cartilage conditions is desirable, particularly agricultural and domestic mammalian species.

The methods of the presently disclosed subject matter are particularly useful in the treatment of warm-blooded vertebrates. Thus, the presently disclosed subject matter concerns mammals and birds.

More particularly, provided herein is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided herein is the treatment of livestock, including, but not limited to, domesticated swine (pigs and hogs), ruminants, horses, poultry, and the like.

V.B. Formulations

In some embodiments, the presently disclosed subject matter also provides pharmaceutical and/or therapeutic compositions comprising the compositions as disclosed herein.

In some embodiments a pharmaceutical composition can also contain a pharmaceutically acceptable carrier or adjuvant. In some embodiments, the carrier is pharmaceutically acceptable for use in humans. The carrier or adjuvant desirably should not itself induce the production of antibodies harmful to the individual receiving the composition and should not be toxic. Suitable carriers can be large, slowly metabolized macromolecules such as proteins, polypeptides, liposomes, polysaccharides, polylactic acids, polyglycolic acids, polymeric amino acids, amino acid copolymers, and inactive virus particles.

Pharmaceutically acceptable salts can be used, for example mineral acid salts, such as hydrochlorides, hydrobromides, phosphates and sulphates, or salts of organic acids, such as acetates, propionates, malonate and benzoates.

Pharmaceutically acceptable carriers in therapeutic compositions can additionally contain liquids such as water, saline, glycerol and ethanol. Additionally, auxiliary substances, such as wetting or emulsifying agents or pH buffering substances, can be present in such compositions. Such carriers enable the pharmaceutical compositions to be formulated for administration to the patient.

Suitable formulations of pharmaceutical compositions of the presently disclosed subject matter include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used. In some embodiments, the carrier is pharmaceutically acceptable. In some embodiments the carrier is pharmaceutically acceptable for use in humans.

Pharmaceutical compositions of the presently disclosed subject matter can have a pH in some embodiments between 5.5 and 8.5, in some embodiments between 6 and 8, and in some embodiments about 7. The pH can be maintained by the use of a buffer. The composition can be sterile and/or pyrogen free. The composition can be isotonic with respect to humans.

Pharmaceutical compositions of the presently disclosed subject matter can be supplied in hermetically-sealed containers.

In some embodiments, the therapeutic methods according to the presently disclosed subject matter comprises administering to a subject in need thereof a composition as disclosed herein.

V.C. Dosages

An effective dose of a pharmaceutical composition of the presently disclosed subject matter is administered to a subject in need thereof. The terms "therapeutically effective amount," "therapeutically effective dose," "effective amount," "effective dose," and variations thereof are used interchangeably herein and refer to an amount of a therapeutic composition or pharmaceutical composition of the presently disclosed subject matter sufficient to produce a measurable response (e.g., reduced symptoms of osteoarthritis). Actual dosage levels can be varied so as to administer an amount that is effective to achieve the desired therapeutic response for a particular subject. In some embodiments, the purpose of introducing the composition of the presently disclosed subject matter is to fill a bone and/or cartilage defect completely or substantially completely, and as such an effective amount would be an amount of a composition of the presently disclosed subject matter that, subsequent to annealing, completely or substantially completely fills the bone and/or cartilage defect.

In some embodiments, the quantity of a therapeutic composition of the presently disclosed subject matter administered to a subject will depend on a number of factors including but not limited to the subject's size, weight, age, the target tissue or organ, the route of administration, the condition to be treated, and the severity of the condition to be treated.

The potency of a therapeutic composition can vary, and therefore a "therapeutically effective" amount can vary. However, using the assay methods described herein below, one skilled in the art can readily assess the potency and efficacy of the pharmaceutical compositions of the presently disclosed subject matter and adjust the therapeutic regimen accordingly.

V.D. Routes of Administration

In some embodiments, the presently disclosed compositions are administered directly to sites of bone and/or cartilage defects and/or damage. In some embodiments, the administration is by direct injection of a composition of the presently disclosed subject matter to a site of bone and/or cartilage defect and/or damage. In some embodiments, the injection is provided arthroscopically or via open surgery. In some embodiments, the composition is administered as part of an open delivery technique, such as open surgery.

EXAMPLES

The following EXAMPLES have been included to provide guidance to one of ordinary skill in the art for practicing representative embodiments of the presently disclosed subject matter. In light of the present disclosure and the general level of skill in the art, those of skill can appreciate that the following EXAMPLES are intended to be exemplary only and that numerous changes, modifications, and alterations can be employed without departing from the scope of the presently disclosed subject matter.

Animals. Animal experiments were performed under a protocol approved by the University of Virginia (Charlottesville, Virginia, United States of America) Institutional Animal Care and Use Committee (Animal Welfare Assurance #A3245-01) in accordance with the United States National Institutes of Health's Guide for the Care and Use of Laboratory Animals. 6-8 week old Sprague-Dawley rats (300-370 g) housed in an AAALAC-accredited facility were utilized.

MAP Scaffold Preparation: Sources/Storage of Materials. Four-arm poly(ethylene glycol) maleimide (PEG-MAL, 10 kDa), four-arm poly(ethylene glycol) thiol (PEG-SH, 10 kDa), and four-arm poly(ethylene glycol) amine (PEG-$NH_2$, 10 kDa) were purchased from Nippon Oil Foundry, Inc. (Japan). RGD cell adhesive peptide (Ac-RGDSPGGC-$NH_2$; SEQ ID NO: 1) was purchased from WatsonBio Sciences (Houston, Texas, United States of America). All materials were dissolved in either ultrapure water or 0.1% Trifluoracetic Acid solutions (to prevent disulfide bond formation) and pre-aliquoted into specified amounts to ensure precision during gel production. The aliquots were lyophilized and stored in −20° C. until preparing aqueous gel solutions. Chondroitin sulfate sodium salt from bovine cartilage (CS) was purchased from Sigma-Aldrich Corp. (St. Louis, Missouri, United States of America).

Example 1

Synthesis of Exemplary Custom Annealing PEG Macromers 6-maledimidohexanoic acid (Sigma-Aldrich; 2.8 mg/mL) and 4-(4,6-Dimethoxy-1,3,5-triazin-2-yl)-4-methylmorpholinium chloride (DMTMM, Oakwood Chemical, Estill, South Carolina, United States of America; 7.4 mg/mL) were combined in ultra-pure water for 30 minutes at room temperature. PEG-$NH_2$ (100.0 mg/mL) and triethylamine (TEA, Thermo Fisher Scientific, Waltham, Massachusetts, United States of America; 4.0 mg/mL) were added and the reaction proceeded for 24 hours. A small volume (50 μL) of the reaction was tested via TNBSA assay (Thermo Fisher Scientific), following the manufacturer's protocol, to ensure at least 25% of amines had reacted. Methacrylic acid (Sigma-Aldrich; 13.8 mg/mL) was mixed with DMTMM (66.4 mg/mL) in ultra-pure water and reacted for 30 minutes, following which the solution was added to the original reaction. Additional TEA (5.4 mg/mL) was added and the reaction proceeded for 24 hours. The solution was again tested via TNBSA assay to ensure all remaining amines had reacted. Following testing, the mixture was transferred into dialysis tubing (3.5K MWCO) and dialyzed into 1M NaCl for 3 days (solution changed daily) then ultra-pure water for 6 hours (solution changed hourly). Final product was frozen at −80° C., lyophilized, and stored at −20° C.

Example 2

Thiolation of Chondroitin Sulfate (CS)

CS (5 mg/mL), 2-aminoethanethiol (Acros Organics, Geel, Belgium; 2.3 mg/mL), and DMTMM (2.8 mg/mL) were dissolved in phosphate buffered saline (1×PBS, pH 6.0) and reacted under rotational agitation for 2 hours at 70° C. Dithiothreitol (DTT, Thermo Fisher Scientific; 12.3 mg/mL) was added and the reaction proceeded at room temperature for 1 hour. The mixture was transferred into dialysis tubing (3.5K MWCO) and dialyzed into 1M NaCl+0.01% trifluoroacetic acid (TFA, Sigma-Aldrich) for 2 hours (solution changed hourly) followed by 0.01% TFA in ultrapure water for 3 hours (solution changed hourly). Final product was frozen at −80° C., lyophilized, and stored at −20° C. Extent of thiolation was determined via Ellman's assay (Thermo Fisher Scientific).

Example 3

Exemplary Pre-gel Solution Formulations

Soft MAP (2 wt %). Solution A: PEG-MAL (45.4 mg/mL gel), RGD (2.12 mg/mL gel), thiolated CS (21.6 mg/mL gel), and a 4-arm PEG annealing reagent (7.55 mg/mL gel) were dissolved in PBS (1×, pH=4.5). Solution B: PEG-SH (21.1 mg/mL gel) and ALEXAFLUOR® 488 (40 μM) were dissolved in ultrapure water.

Stiff MAP (10 wt %). Solution A: PEG-MAL (125 mg/mL gel), RGD (2.12 mg/mL gel), thiolated CS (21.6 mg/mL gel), and an annealing reagent (7.55 mg/mL gel) were dissolved in PBS (1×, pH=4.5). Solution B: PEG-SH (97.3 mg/mL gel) and ALEXAFLUOR® 488 (40 μM) were dissolved in ultrapure water.

Solution A and Solution B were mixed in equal parts to form the aqueous pre-gel solutions. All references to gel weight percent are describing gel backbone weight percent during gelation.

Example 4

Macrogel Production and Mechanical Testing

Macro-scale gels (i.e., macrogels) were used to determine hydrogel stiffness (Sideris et al., 2016). Macrogels were synthesized using pre-gel formulations described above. 200 gel pucks were formed between SIGMACOTE® brand siliconizing reagent (MilliporeSigma, Burlington, Massachusetts, United States of America) coated slides and gelation proceeded for 1 hour at room temperature. 10 TEA was pipetted onto the edge of the macrogels to force gelation to completion. The macrogels were collected after 30 minutes and swollen to equilibrium in PBS (1×, pH=7.4) for a minimum of 1 hour prior to testing. An Instron mechanical load device was used to test compressive stiffness (Young's modulus) at a rate of 0.5 mm/min for 1 minute and BLUEHILL® software analyzed the load (N) and extension (mm). Stress-strain curves were produced and the Young's modulus (Pa) was calculated using Excel (Microsoft Office, version 16, Microsoft Corporation, Redmond, Washington, United States of America).

Example 5

Macrogel Production and Purification 350 mL of Light Mineral Oil (Fisher) supplemented with 1% Span80 (TCI Chemicals, Burlington, Massachusetts United States of America) was mixed in a 600 mL graduated cylinder with an overhead rotor (IKA EuroStar 20 Digital; IKA Works, Inc., Wilmington, North Carolina, United States of America) at 300 rpm using spiral stirrer (IKA R3003). After 20 minutes of stirring, TEA was added at 20 μL/mL of total pre-gel via pipette. Five minutes later, aqueous pre-gel solution was then injected into the stirring oil solution at 2.5 mL/hr using a syringe pump (KD Scientific Inc., Holliston, Massachusetts United States of America). Following injection, the rotor was stopped, and the microgels were allowed to settle overnight before collection using centrifugation (5 minutes×4696 g). Sequential light mineral oil washes (~20× gel volume for four washes) were performed to remove the surfactant (Töyräs et al., 2001). The mixture was then purified by adding the gel-oil solution onto an equal volume of PBS and collecting via high speed centrifugation (5 minutes×18000 g). Microgels were sterilized with 70% isopropanol (~10× gel volume for three washes) and stored in 70% isopropanol at 4° C. until use. All PBS for microgel purification and preparation refers to 1×PBS, pH=7.4.

Example 6

Preparation of Exemplary CartilageMAP Compositions

To facilitate annealing of the cartilage-like scaffold, Stiff MAP was seeded with Soft MAP (3:1). Stiff and Soft MAP were equilibrated in sterile PBS (~10× gel volume for three washes) and dried (1 minutes×500 g) using centrifuge filter tubes (0.22 μm; Corning-Costar Corp., Cambridge, Massachusetts, United States of America). The mass of the dried Stiff MAP was recorded, and Soft MAP was added to achieve a 3:1 mass ratio. Combined microgels were resuspended in sterile PBS, vortexed for 30 seconds, and collected via centrifugation (5 minutes×4696 g), yielding a microporous gel system referred to herein as "Cartilage-MAP" ready for application. A small volume (10 μL) of concentrated microgels was reserved for sizing. The remaining CartilageMAP was resuspended in sterile PBS+40 μM Eosin Y (Acros Organics; —3× gel volume). To prepare microgels for surgical injection, the CartilageMAP preparation was dried and transferred into a sterile syringe (1 mL; Becton, Dickinson and Company, Franklin Lakes, New Jersey, United States of America) using a positive displacement pipette (MicroMan; Gilson Inc., Middleton, Wisconsin, United States of America). Loaded syringes were stored at 4° C. until use.

Example 7

Microgel Size Characterization

Microgel spherical diameter was determined using fluorescent images of a dilute solution (1:100) of microgels and ImageXpress based quantification (Molecular Devices, LLC., San Jose, California, United States of America). A minimum of 500 microgels (N) were analyzed to determine average diameter (D) and polydispersity index (PDI). The number average was calculated by DN=Σ NiDi/Σ Ni and weight average was calculated by DW=Σ NiDi2/Σ NiDi. PDI was calculated by Dw/DN. The average combined microgel size was 50.8±22.8 μm with a PDI of 1.39.

Example 8

Surgical Procedure

Figure 1B:
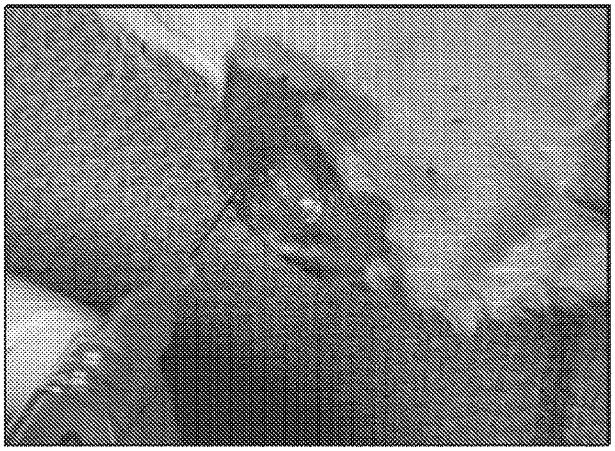
Figure 1C:
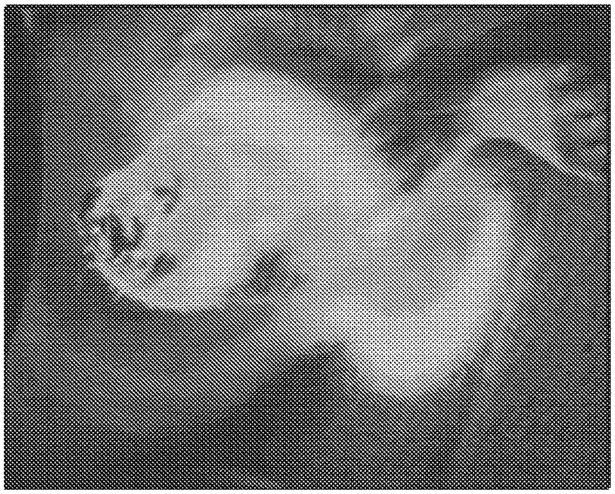

Eighteen Sprague-Dawley rats underwent surgical creation of knee osteochondral defects (n=36 knees). Two experimental groups were created, a negative control group with saline within the OCD, and a MAP gel group (n=18 saline control knees, n=18 MAP treated knees). A previously established rat knee osteochondral defect model disclosed in Frohbergh et al., 2016 was employed. The rats were anesthetized (2.5% inhaled isoflurane), and both legs/knees were shaved, prepared with betadine and draped for aseptic surgery. A medial parapatellar incision was made through the skin, fascia and joint capsule. The patella was reflected laterally to expose the trochlear surface of the femur. A 2.5 mm diameter 2.5 mm deep osteochondral defect was created in the trochlea using an electric drill, fitted with a depth indicated engraving cutter bit (#107; Dremel, Racine, Wisconsin, United States of America). See FIGS. 1A and 1B. This was repeated for the contralateral knee. There were two experimental groups—in the negative control group, the osteochondral defect was filled with saline alone, in the experimental group the osteochondral defect was filled with 30-50 μL of injectable MAP gel conjugated to chondroitin sulfate using a 23 gauge blunt tipped needle. Microgels were annealed with a 505 nm LED light (DC2200, M505L3-C1; Thorlabs Inc., Newton, New Jersey, United States of America) for 10 minutes (1000 mA, 5 cm distance from gel). See FIG. 1C. The patella was replaced and the fascia and skin were reapproximated. Upon completion, the joint capsule and skin closed with 4-0 VICRYL® sutures.

Example 9

Histological Analyses

Histological analysis was performed at 2 week, 4 week, and 8 week post-operative time points. At each time point, animals were euthanized and the femoral heads were harvested. The specimens were placed into Formical-2000 (Fisher Scientific) and gently rocked for 6 days, and embedded in paraffin. Specimens were then cross-sectioned through the osteochondral defect. Five-micron sections were stained with (1) hematoxylin and eosin (H&E) to evaluate tissue architecture and cellular infiltration and (2) safranin-O to quantify glycosaminoglycan expression.

Example 10

Production of Exemplary MAPs from Soft and Stiff Microgels

Attempts to form MAP gel entirely of the Stiff microgels would not anneal to form a solid scaffold. By mixing soft microgels and stiff microgels together at a 1:3 ratio a scaffold that was injectable and annealed properly was achieved. Young's moduli of Stiff and Soft MAP microparticles were 94.7 kPa (matched to cartilage range; Töyräs et al., 2001) and 6.2 kPa, respectively. The average combined microgel size was 50.8±22.8 μm with a PDI of 1.39.

Example 11

Treatment of Osteochondral Defects with MAPS

Figure 2B:
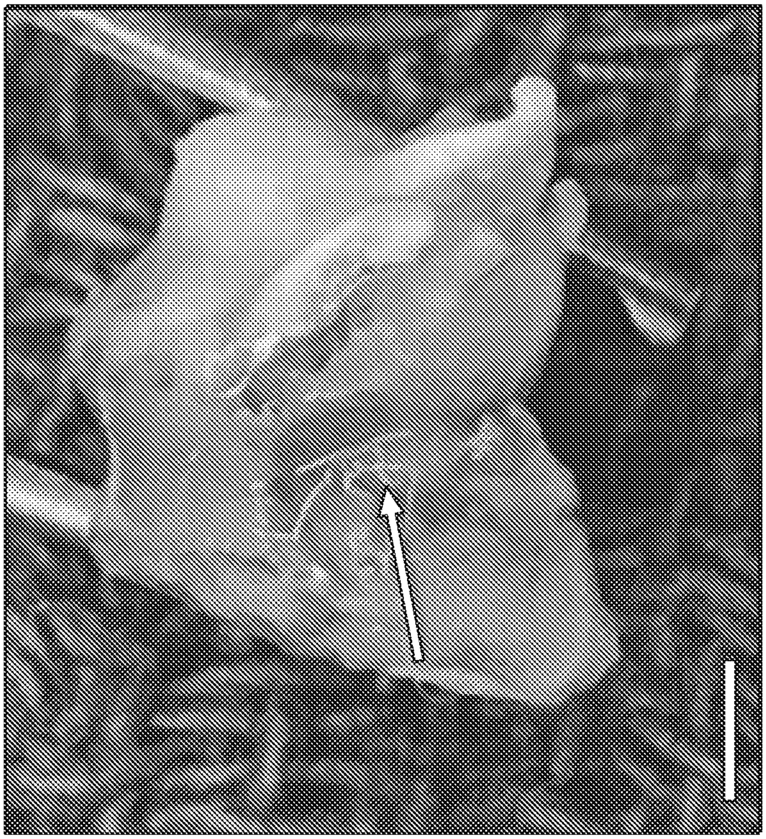
FIGS. 2A and 2B are gross photographs of the defects treated with saline and MAP gel, harvested at 8 weeks post-operatively.
Figure 2A:
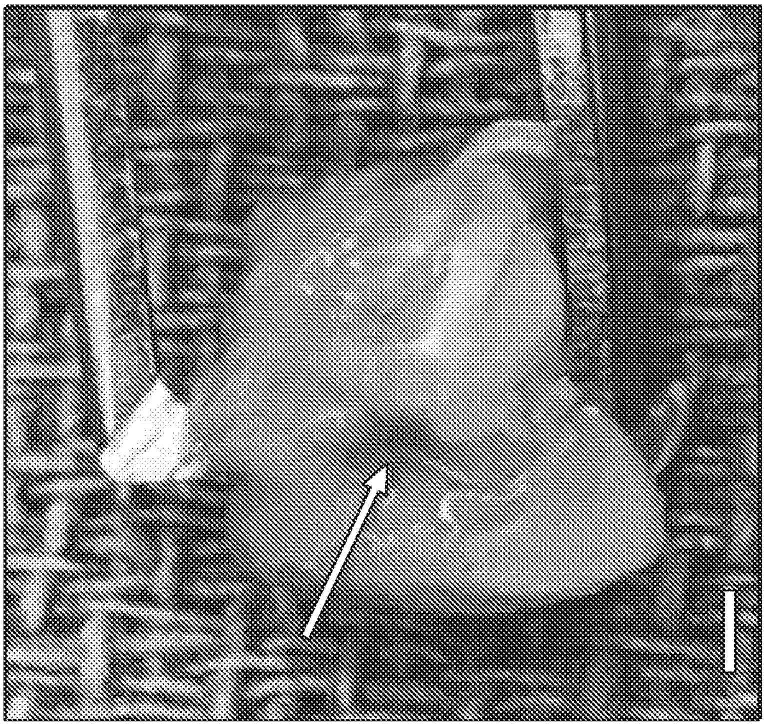
Figure 3A:
FIGS. 3A-3C present representative H&E stained sections.
Figure 3B:
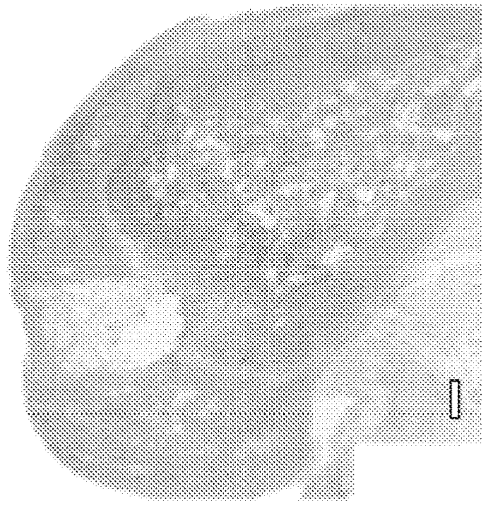
Figure 3C:
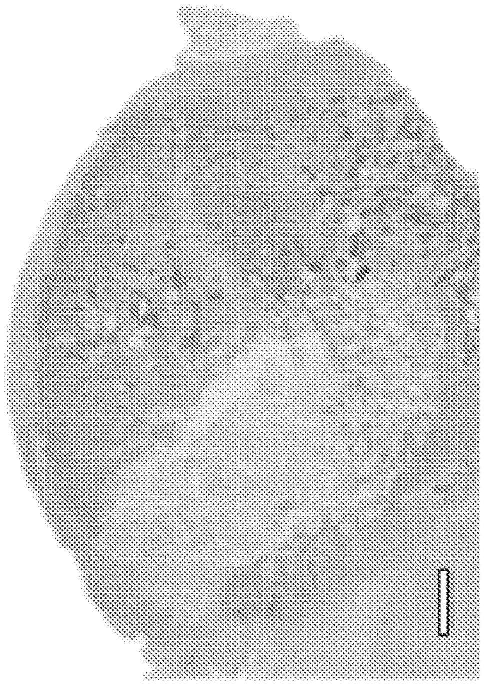

Gross photographs taken at 2 week, 4 week, and 8 week time points demonstrated qualitative evidence of reduced scar formation around the defects in the MAP treated knees compared to the saline treated knees. See FIGS. 2A and 2B. Histologic analysis was also performed at the 2 week, 4 week, and 8 week time points (n=6 at each time point). H&E staining demonstrated persistence of the MAP gel within the osteochondral defect through the entire 8 week experiment. See FIGS. 3A-3C. In MAP treated knees (FIGS. 3B and 3C), the persistence of the scaffold allowed for the maintenance of a smooth surface, providing host cell migration and ensuring a more normal architecture. In addition, there was evidence of host integration with tissue deposition, and minimal inflammatory response. In the saline treated defects (FIG. 3A), the overall architecture of the articular surface appeared contracted with scar formation and osseous ingrowth, leading to a non-smooth surface. Safrinin-O staining showed evidence of increased glycosaminoglycan (GAG) expression within the MAP scaffold compared to the control. Additionally, there was evidence of GAG rich tissue migrating across the MAP gel surface during healing. See FIGS. 4A-4C.

Discussion of the Examples

In this use of the MAP gel as a regenerative scaffold in a small animal osteochondral defect model, the feasibility of delivery and annealing of an injectable, flowable scaffold to a clinically relevant critical cartilage defect model has been demonstrated. The gel was found to fill the defect and the gel demonstrated object permanence with maintenance of its structure and position up to the 8 week time point. Of note, in control treated cartilage defects without treatment with MAP gel, the osteochondral defects appeared to contract and fill with scar and subchondral bone.

Figure 4C:
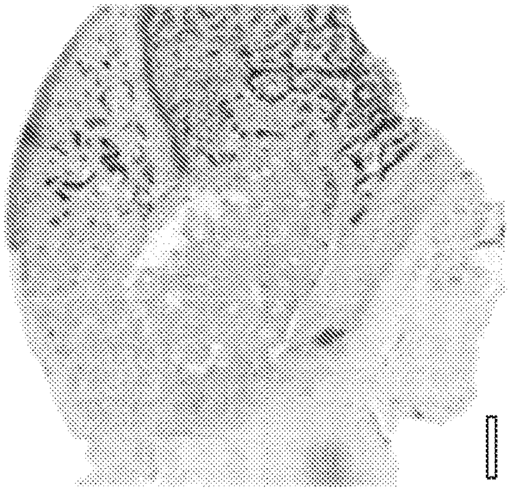
FIGS. 4A-4C are representative safranin-O-stained sections of defects.
Figure 4B:
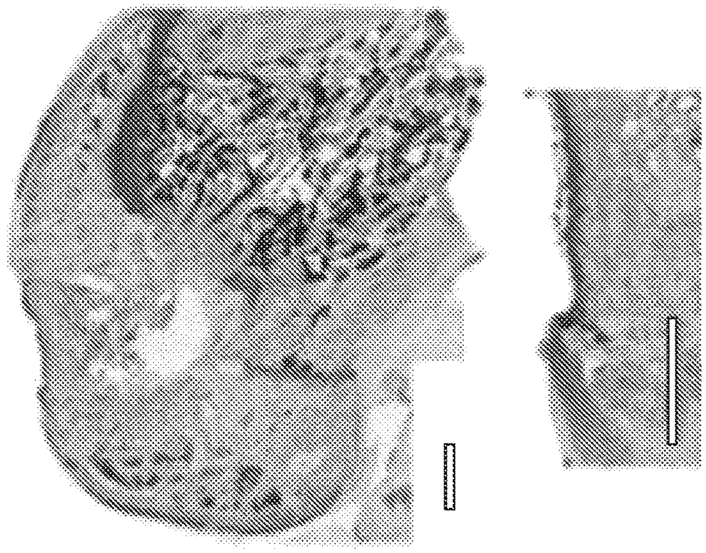
Figure 4A:
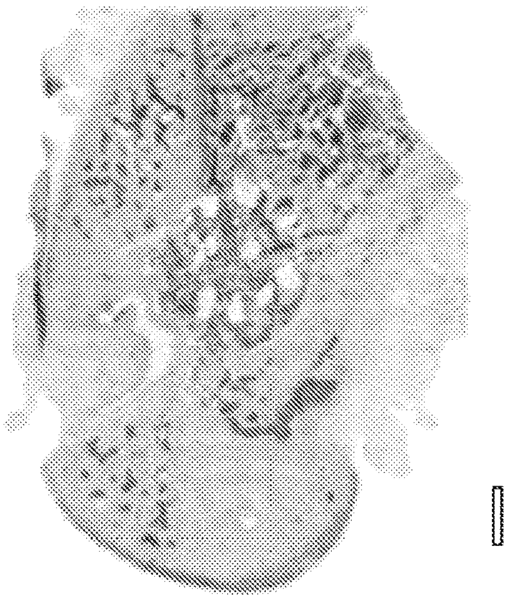

Histologic evaluation showed the lack of an inflammatory response to the MAP gel and excellent tissue integration (see FIGS. 4A-4C). Glycosaminoglycan rich tissue, found in cartilage, was also noted to migrate across the surface of the MAP gel, which could signify a re-establishment of the previously damaged articular cartilage across the defect (see FIGS. 4A-4C).

It is unclear at this time the clinical significance of the MAP gel maintaining the width and depth of the osteochondral defect; however, it is hypothesized that this feature allows the MAP gel to provide a stable scaffold for more organized deposition of host tissue. However, definitive cartilaginous ingrowth within the gel has not been absolutely confirmed on histologic evaluation. Nonetheless, the presently disclosed subject matter successfully demonstrated the feasibility of utilizing a base formulation of a MAP gel that provide a stiffness matched to articular cartilage as an effective scaffold in an osteochondral defect. The “plug and play” nature of the MAP gel provides the option of further tuning the mechanical properties and to incorporate key signaling extracellular cellular matrix components, cytokines, growth factors, and cells, such as chondroitin sulfate, TGF-β, and mesenchymal stem cells, or chondrocytes to promote cartilaginous ingrowth and augment its efficacy.

A major limitation of biomaterial-based approaches to cartilage regeneration to date is lack of mechanical integration. A benefit to this porous biomaterial is an accelerated window of tissue-biomaterial integration, which is illustrated by maintenance of the gel within the osteochondral defect with host tissue deposition at the 8 week time point as disclosed herein. Additionally, current approaches to cartilage regeneration (osteochondral allograft transplantation) and surgical management of end-stage wrist arthritis (arthroplasty or arthrodesis) necessitate open approaches to the joint. With these open approaches, there is morbidity associated with violation of the joint capsule including discomfort, bleeding, and scar formation. MAP is the first flowable porous biomaterial scaffold, making it an ideal candidate for arthroscopic procedures (e.g. wrist arthritis treatment), which represents a fundamental change in the approach to cartilage replacement or reconstruction.

Summarily, disclosed herein is the demonstration of successful delivery of an injectable, flowable MAP gel scaffold into a rat knee osteochondral defect with subsequent annealing and stable positioning. The flowable nature of this scaffold allowed for minimally invasive application, for example via an arthroscopic approach for management of wrist arthritis. The MAP gel was noted to fill the osteochondral defect and maintain the defect dimensions, suggesting its ability to provide a stable scaffold for tissue ingrowth. The MAP gel did not elicit a chronic inflammatory response and maintained a structurally smooth surface that allowed for GAG-rich tissue to migrate across. Thus, the presently disclosed demonstration of feasibility provides opportunity for optimized MAP gel formulations to promote the healing of articular cartilage and increase the treatment options for patients with osteoarthritis.

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference.

Armiento et al. Biomaterials for articular cartilage tissue engineering: Learning from biology. Acta Biomater. 2018; 65:1-20.

Frohbergh et al. Acid ceramidase treatment enhances the outcome of autologous chondrocyte implantation in a rat osteochondral defect model. Osteoarthr Cartil. 2016; 24(4):752-762.

Griffin et al. Accelerated wound healing by injectable microporous gel scaffolds assembled from annealed building blocks. Nat Mater. 2015; 14(7):737-744.

Medved et al. Severe posttraumatic radiocarpal cartilage damage: First report of autologous chondrocyte implantation. Arch Orthop Trauma Surg. 2013; 133(10):1469-1475.

Mobasheri et al. Chondrocyte and mesenchymal stem cell-based therapies for cartilage repair in osteoarthritis and related orthopaedic conditions. Maturitas. 2014; 78(3): 188-198.

Murphy et al. Medical Expenditures and Earnings Losses Among US Adults With Arthritis in 2013. Arthritis Care Res. 2018; 70(6):869-876.

Obert et al. Rib Cartilage Graft for Posttraumatic or Degenerative Arthritis at Wrist Level: 10-Year Results. J Wrist Surg. 2013; 02(03):234-238.

PCT International Patent Application Publication Nos. 2016/011387; 2019/200390.

Sideris et al. Particle Hydrogels Based on Hyaluronic Acid Building Blocks. ACS Biomater Sci Eng. 2016; 2(11): 2034-2041.

Töyräs et al. Estimation of the Young’s modulus of articular cartilage using an arthroscopic indentation instrument and ultrasonic measurement of tissue thickness. J Biomech. 2001; 34(2):251-256.

U.S. Patent Application Publication Nos. 2016/0279283, 2017/0368224, 2018/0078671, and 2019/0151497.

U.S. Pat. No. 9,447,381.

Yang et al. Development of chondrocyte-seeded electrosprayed nanoparticles for repair of articular cartilage defects in rabbits. J Biomater Appl. 2018; 32(6):800-812.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A composition comprising at least one sub-population of soft hydrogel microparticles with a Young's modulus of less than 50 kPa and at least one sub-population of stiff hydrogel microparticles with a Young's modulus of greater than 90 kPa.

2. The composition of claim 1, wherein the composition further comprises an annealing initiator, a small molecule crosslinker; a soluble crosslinker; a heat-activated crosslinker; a spontaneous radical generating crosslinker combination; and an enzymatic crosslinker, wherein the annealing initiator facilitates annealing of the at least one soft hydrogel and the at least one stiff hydrogel to form a microporous annealed particle (MAP) scaffold.

3. The composition of claim 2, wherein the annealing initiator comprises a photoinitiator that is selected from the group consisting of Eosin-Y and lithium phenyl-(2,4,6-trimethyl benzoyl) phosphinate (LAP).

4. The composition of claim 2, wherein the spontaneous radical generating crosslinker combination comprises ammonium persulfate combined with tetramethylethylenediamine.

5. The composition of claim 2, wherein the enzymatic crosslinker is Factor XIII.

6. The composition of claim 1, wherein both the at least one sub-population of soft hydrogel microparticles and at least one sub-population of stiff hydrogel microparticles comprise one or more methacrylamide functionalities that permit inter-microparticle surface chemical annealing of at least one soft hydrogel microparticle and at least one stiff hydrogel microparticle to create a microporous annealed particle (MAP) scaffold.

7. The composition of claim 1, wherein the volume of the at least one soft hydrogel microparticle sub-population present in the composition is in a ratio of 1:10 to 1:3 with respect to the volume of the at least one stiff hydrogel microparticle sub-population in the composition.

8. The composition of claim 1, wherein the at least one soft hydrogel microparticle sub-population, the at least one stiff hydrogel microparticle sub-population, or both comprise a polyethylene glycol (PEG).

9. The composition of claim 8, wherein the at least one soft hydrogel microparticle sub-population, the at least one stiff hydrogel microparticle sub-population, or both comprise a PEG with an average molecular weight of 10 kiloDaltons (kDa).

10. The composition of claim 1, wherein the composition further comprises one or more additional active agents.

11. The composition of claim 10, wherein the one or more additional active agents are selected from the group consisting of a cell adhesive peptide, chondroitin sulfate (CS), heparin, and combinations thereof.

12. The composition of claim 11, wherein the cell adhesive peptide comprises an RGD-containing cell adhesive peptide.

13. The composition of claim 12, wherein the RGD-containing cell adhesive peptide comprises, consists essentially of, or consists of the amino acid sequence RGDSPGGC (SEQ ID NO: 1).

14. The composition of claim 10, wherein the chondroitin sulfate (CS) is thiolated CS.

15. A method for generating a microporous gel system, the method comprising:

(a) combining at least one soft hydrogel microparticle sub-population with a Young's modulus of less than 50 kPa and at least one stiff hydrogel microparticle sub-population with a Young's modulus of greater than 90 kPa to create a mixture; and (b) annealing the at least one soft hydrogel microparticle sub-population and the at least one stiff hydrogel microparticle sub-population in the mixture, whereby a microporous gel system is generated.

16. A method for treating a bone and/or cartilage defect in a subject, the method comprising introducing into the bone and/or cartilage defect a composition of claim 1 in an amount sufficient to substantially or completely fill the bone and/or cartilage defect, and annealing the at least one soft hydrogel and the at least one stiff hydrogel present in the composition such that a microporous annealed particle (MAP) scaffold is produced in the bone and/or cartilage defect.

* * * * *